US006458578B1

(12) United States Patent
Brough et al.

(10) Patent No.: US 6,458,578 B1
(45) Date of Patent: Oct. 1, 2002

(54) RECOMBINANT CELL LINE PRODUCES ADENOVIRAL GENE PRODUCTS E1 AND DEF-A, AND/OR DEF-B

(75) Inventors: Douglas E. Brough, Olney; Imre Kovesdi, Rockville, both of MD (US)

(73) Assignee: GenVec, Inc., Gaithersburg, MD (US)

( * ) Notice: Subject to any disclaimer, the term of this patent is extended or adjusted under 35 U.S.C. 154(b) by 101 days.

(21) Appl. No.: 09/748,044

(22) Filed: Dec. 22, 2000

Related U.S. Application Data

(63) Continuation of application No. PCT/US99/14333, filed on Jun. 24, 1999, which is a continuation-in-part of application No. 09/105,515, filed on Jun. 26, 1998, now Pat. No. 6,113,913.

(51) Int. Cl.$^7$ .............................. C12N 7/00; C12N 7/01; C12N 15/00; A61K 39/235; A61K 39/12
(52) U.S. Cl. .................... 435/235.1; 435/325; 435/69.1; 435/320.1; 424/233.1; 424/199.1
(58) Field of Search .............................. 435/325, 235.1, 435/69.1, 320.1; 424/233.1, 199.1

(56) References Cited

U.S. PATENT DOCUMENTS

| 4,510,245 A | 4/1985 | Cousens et al. |
| 5,474,935 A | 12/1995 | Chatterjee et al. |

FOREIGN PATENT DOCUMENTS

| FR | 2 707 664 A | 1/1995 |
| WO | WO94/24297 A | 10/1994 |
| WO | WO95/29993 A | 11/1995 |
| WO | WO95/34671 A | 12/1995 |
| WO | WO96/14061 A | 5/1996 |

OTHER PUBLICATIONS

Amalfitano et al., *Gene Ther.*, 4, 258–263 (1997).
Amalfitano et al., *J. Virol.*, 72 (2), 926–933 (1998).
Amalfitano et al., *PNAS USA*, 93, 3352–3356 (1996).
Brunet et al., *Mol. Cell. Biol.*, 7 (3), 1091–1100 (1987).
Chodosh et al., *Mol. Cell. Biol.*, 6 (12), 4723–4733 (1986).
Gustin et al., *J. Virol.*, 70 (9), 6463–6467 (1996).
Kubo et al., *Gene*, 153, 279–280 (1995).
Lieber et al., *J. Virol.*, 70 (12), 8944–8690 (1996).
Loh et al., *J. Biol. Chem.*, 271 (18), 10884–10891 (1996).
Lu et al., *J. Virol.*, 71 (1), 102–109 (1997).
Lutz et al., *J. Virol.*, 70 (3), 1396–1405 (1996).
Lutz et al., *J. Virol.*, 70 (6), 3449–3460 (1996).
Manohar et al., *J. Virol.*, 64 (6), 2457–2466 (1990).
Miyamoto et al., *EMBO J.*, 4(13A), 4563–3570 (1985).
Perlmutter et al., *Clin. Exp. Pharmacol. Physiol.*, 17, 697–706 (1990).
Reach et al., *J. Virol.*, 64 (12), 5851–5860 (1990).
Reach et al., *EMBO J.*, 10 (11), 3439–3446 (1991).
Sawadago et al., *Cell*, 43, 165–175 (1985).
Schaack et al., *J. Virol.*, 69 (7), 4079–4085 (1995).
Song et al., *Virology*, 220 (2), 390–401 (1996).
Strubin et al., *Cell*, 68, 721–730 (1992).
Tansey et al., *Science*, 275 (5301), 829–831 (1997).
Tribouley et al., *J. Virol.*, 68 (7), 4450–4457 (1994).
Van Beveren et al., *Gene*, 16, 179–189 (1981).
Wilkinson et al., *Nucl. Acids Res.*, 20 (9), 2233–2239 (1992).
Wu et al., *Biotechniques*, 21, 718–725 (1996).
Yang et al., *PNAS USA*, 91 (10), 4407–4411 (1994).

*Primary Examiner*—Ali R. Salimi
(74) *Attorney, Agent, or Firm*—Leydig, Voit & Mayer, Ltd.

(57) ABSTRACT

The present invention provides a recombinant cell line, specifically one that produces adenoviral E1 and DEF-A and/or DEF-B gene products.

4 Claims, No Drawings

RECOMBINANT CELL LINE PRODUCES ADENOVIRAL GENE PRODUCTS E1 AND DEF-A, AND/OR DEF-B

CROSS-REFERENCE TO RELATED APPLICATIONS

This is a continuation of International Patent Application PCT/US99/14333, filed on Jun. 24, 1999, designating, inter alia, the United States of America and which is a continuation-in-part of U.S. patent application Ser. No. 09/105,515, filed Jun. 26, 1998, now U.S. Pat. No. 6,113,913.

TECHNICAL FIELD OF THE INVENTION

The present invention relates to a recombinant cell line, specifically one that produces adenoviral E1 and DEF-A and/or DEF-B gene products.

BACKGROUND OF THE INVENTION

Modified adenoviruses have proven convenient vector systems for investigative and therapeutic gene transfer applications, and adenoviral viral systems present several advantages for such uses. The development of adenoviral vectors rests on an understanding of viral genetics and molecular biology. Structurally, all adenoviral virions are nonenveloped capsids with a number of surface proteins. Through interactions of these capsid proteins with the surface of a host cell, the virus is internalized and encased in an clathrin-coated organelle resembling an endocytotic vessel (Pastan et al., *Concepts in Viral Pathogenesis*, Notkins and Oldstone, eds.

Springer-Verlag, New York. pp. 141–46 (1987)). The acidic condition within the vesicle alters the surface configuration of the virus, resulting in vesicle rupture and release of the virus into the cytoplasm of the cell, where it is partially freed of associated proteins while being transported to the nucleus. Once an adenoviral genome is within the host cell nucleus, its expression proceeds through a highly ordered and well characterized cascade. Groups of adenoviral genes (i.e., translation units) are typically organized into common transcription units ("regions"), each having at least one distinct promoter. The transcript from each region is processed after transcription to generate the multiple mRNA species corresponding to each viral gene. Generally, the separate regions are either "early" or "late," although some genes are expressed as early and late.

Cellular transcription factors first bind to the upstream enhancer of the first early (E1A) region of the adenoviral genome. The E1A gene products, in turn, regulate the expression of other early promoters, one of which (E2B) drives the expression of the transcription unit including three early genes involved in adenoviral DNA replication (Doefler, pages 1–95, in *Adenovirus DNA, the Viral Genome, and Expression*, Nojhoff, Boston, (1986)). These three proteins (the precursor terminal protein (pTP), the single-stranded DNA binding protein (ssDBP), and the DNA polymerase (pol)) form a tight unit with at least three cellular proteins to drive priming and elongation of the viral genome (Bodnar et al., *J. Virol.*, 63, 4344–53 (1989); Schnack et al., *Genes Devel.*, 4, 1197–1208 (1990); Pronk et al., *Clomosoma*, 102, S39–S45 (1992); Kelly et al., pages 271–308, in *The Adenoviruses* (H. S. Ginsberg, ed.), Plenum Press, New York (1984)).

Once viral DNA replication commences, the activity of the early promoters declines (Sharp et al., pages 173–204, in *The Adenoviruses* (H. S. Ginsberg, ed.), Plenum Press, New York (1984)), as does the expression of cellular genes, due to the activity of the viral host shut-off early gene products. Conversely, promoters controlling the expression of the late genes become active beginning with the onset of viral DNA replication (Thomas et al., *Cell*, 22, 523–33 (1980)). Indeed, DNA replication appears necessary for the expression of some late genes. For example, while the major late promoter (MLP) exhibits some activity at early times, only the promoter proximal genes are expressed (Shaw et al., *Cell*, 22, 905–16 (1980); Winter et al., *J. Virol.*, 65, 5250–59 (1991)). However, the activity of the MLP sharply increases following the onset of viral DNA replication (Shaw et al., supra), resulting in the expression of all the MLP gene products (Doeller et al., supra; Thomas et al., supra; Nevins et al., *Nature*, 290, 113–18 (1981)). The structure of this promoter has been extensively characterized (see, e.g., Lu et al., *J. Virol.*, 71(1), 102–09 (1997); Lutz et al., *J. Virol.*, 70(3), 1396–1405 (1996); Reach et al., *EMBO J.*, 10(11), 3439–46 (1991); Reach et al., *J. Virol.*, 64(12), 5851–60 (1990); Brunet et al., *Mol. Cell. Biol.*, 7(3), 1091–1100 (1987); Miyamoto et al., *EMBO J.*, 4, 3563–70 (1985)). In particular, the MLP of the Ad5 serotype has three upstream promoter elements, two downstream elements and an initiator element (INR, SEQ ID NO:1) located at the start site. The three upstream elements are an inverted CAAT box (i.e., GTTA) located 76 base pairs upstream of the start site, an upstream promoter element (UPE, SEQ ID NO:2) located 63 base pairs upstream of the start site, and the TATA box (sequence: TATAAAA), located 31 base pairs upstream of the start site. The two downstream elements are DE1 (SEQ ID NO:3), located 86 base pairs downstream of the start site, and DE2 (SEQ ID NO:4), located 101 base pairs downstream of the start site. These various promoter elements interact with viral and cellular proteins to drive late transcription of the MTLU. For example, two proteins (DEF-A and DEF-B) bind to the downstream elements in a late-phase-dependent manner. DEF-B has been identified as the product of adenovirus intermediate gene IVa2 (pIVa2) (Tribouley et al., *J. Virol*, 68, 4450–57 (1994)), which has been cloned (van Beveren et al., *Gene*, 16, 179–89 (1981)). In addition, as mentioned, E1A gene products drive some MLP activity during the early stage of infection Post-transcriptional processing of the major late transcription unit (MTLU) gives rise to five families of late mRNA, designated respectively as L1 to L5 which encode structural components of the viral capsid (Shaw et al., *Cell*, 22, 905–916 (1980)). These proteins are highly toxic to cells, and they can potentiate immune responses against infected cells (see, e.g., Yang et al., *Proc. Nat. Acad. Sci.* (*USA*), 91, 4407–11 (1994)). This immune response leads to tissue swelling and destruction of the transduced cells, shortening the period of time transgenes are expressed in the cells. "First generation" adenoviral vectors have been engineered to silence the adenoviral genome with the aim of reducing these deleterious effects. Because, as mentioned, the E1A gene products begin the cascade of viral gene expression, the earliest adenoviral vectors lacked functional E1A regions. For example, insertion of an exogenous gene into the E1 region results in recombinant vectors that can express the exogenous gene but not the E1A gene. The recombinant adenoviruses must be propagated either in complementary cells or in the presence of a helper virus to supply the impaired or absent essential E1 products (Davidson et al., *J. Virol.*, 61, 1226–39 (1987); Mansour et al., *Mol. Cell Biol.*, 6, 2684–94 (1986)).

While such first generation viruses have proven effective in several gene transfer applications, they are not optimal for all uses. In particular, because they must be grown in the presence of E1 complementing DNA, at some frequency recombination events can generate a replication competent adenovirus (RCA). RCA contamination of viral stocks is problematic because RCAs can outgrow recombinant stocks and transform host cells. Moreover, at higher multiplicity of infections (m.o.i.s), several adenoviral promoters are active even in the absence of the E1A gene products, which can lead to the production of cytotoxic adenoviral proteins (Nevins, *Cell*, 26, 213–20 (1981); Nevins et al., *Curr. Top. Microbiol. Immunol.*, 113, 15–19 (1984)). An additional disadvantage of first generation vectors is largely attributable to this background expression of late gene products. For example, such residual late gene expression can potentiate host immune responses eliminating virally transduced cells (see, e.g., Yang et al., supra; Gilgenkrantz et al., *Hum. Gene. Ther.*, 6, 1265–74(1995); Yang et al., *J. Virol.*, 69, 2008–15 (1995); Yang et al., *J. Virol.*, 70, 7209–12 (1996)).

One approach for blocking late gene expression is to selectively block viral replication by mutating the virus such that it fails to express one or more of the three E2B enzymes involved in viral DNA replication. However, while E1A-deficient viruses lacking E2B function can be generated, the approach requires the use of complementing cell lines or helper viruses to supply the missing essential gene product (Almafitano, *J. Virol.*, 72(2), 926–33 (1998)). As discussed above, a major drawback to such an approach is that recombination events within packaging cells between such vectors and complementing genes can generate RCAs. Moreover, of the three E2B genes, it is not currently possible to propagate a virus lacking the ssDBP gene entirely because the required co-expression of the complementing ssDBP and E1A gene products in the same packaging cell is lethal (Klessig et al., *Mol. Cell Biol.*, 4, 1354–62 (1984)). A vector has been constructed that has a temperature sensitive mutation in the ssDBP gene (Engelhardt et al., *Proc. Nat. Acad. Sci. (USA)*, 91, 6196–6200 (1994)). In some systems, this vector has resulted in longer gene expression and reduced immune-inflammatory response than first generation vectors (Yang et al., *Proc. Nat. Acad. Sci. (USA)*, 92, 7257–61 (1995); Engelhardt et al., *Hum. Gene Ther.*, 5, 1217–29 (1994)). However, the temperature-sensitive mutation is imperfect, permitting some basal ssDBP activity at core body temperature, especially at high m.o.i.s (Yang et al., *Proc. Nat. Acad. Sci. (USA)*, 92, 7257–61 (1995)). In addition to these drawbacks, the approach of disrupting the E2B region also impacts the MTLU because the three E2B genes lie on the chromosomal strand directly opposite the L1–L5 genes and the MLP, (see, e.g., Almafitano et al., *Gene Ther.*, 4, 258–63 (1997)).

In view of the foregoing problems, there exists a need for a recombinant adenovirus, specifically a virus exhibiting reduced propensity to generate RCAs within packaging cells and less able than first generation vectors to express late viral gene products in a host cell.

BRIEF SUMMARY OF THE INVENTION

The present invention addresses the aforementioned need by providing a recombinant adenovirus which, aside from lacking E1 gene expression, has a mutated MLP. The mutation in the MLP greatly attenuates L1–L5 gene expression in nonpermissive host cells. Thus, such recombinant adenoviruses are less able than first generation vectors to express late viral gene products in a host cell. Moreover, many such recombinant adenoviruses can be grown in packaging cells without the presence of DNA complementary to the wild-type adenoviral MLP, thus substantially reducing the probability for generating RCAs.

The present inventive recombinant adenoviruses will prove highly useful in biological research. Specifically, the invention provides reagents and methods enabling biologists to more easily study viral molecular genetics and cytotoxicity. Additionally, the present invention provides reagents and methods pennitting biologists to investigate the cell biology of viral growth and infection. Furthermore, the recombinant adenoviruses of the present invention will equip the biologist with novel tools for investigating molecular and cellular biology of gene expression and regulation in novel genetic backgrounds. Such studies, for example, can focus on the interaction between gene products in a defined or selected cellular background, the ability of transcription factors to transregulate gene expression via promoter, repressor, or enhancer elements engineered into the adenovirus, etc. The present inventive recombinant adenoviruses also will prove highly useful as gene transfer vehicles for research or in the clinical setting. Specifically, the adenovirses of the present invention are useful vectors for introducing transgenes into tissue culture cells or into the cells of animals to study development or repair of tissues. The vectors will find application as well in treating diseases through the transfer of therapeutic genes.

These and other advantages of the present invention, as well as additional inventive features, will be apparent from the following detailed description.

DETAILED DESCRIPTION OF THE INVENTION

As used herein, including the claims appended hereto, the following terms are employed as follows:

An adenovirus refers to any virus of the genus adenoviridae, regardless of host species specificity or viral serotype. However, for clarity and ease of reference, the present invention will be described with reference to the Ad5 serotype.

A packaging cell is a cell able to propagate recombinant adenoviruses by supplying a product required for efficient viral growth. For example, where a recombinant adenovirus contains deficiencies in one or more genes essential for efficient replication, the packaging cell expresses the missing viral gene product, either from its own genome or from a gene located on a vector within the cell (e.g., a plasmid, a "helper virus," etc.).

A gene is defined as a DNA or RNA sequence corresponding to (i.e., encoding) a mature RNA species. In many cases, a gene encodes a protein; however, some gene products are active as mature RNA (e.g., rRNA, antisense RNA, ribozymes, etc.).

Mutation is broadly defined to mean any change from a DNA sequence native to the stereotype from which the recombinant adenovirus is derived. Such mutations can be the deletion of at least one nucleotide from the native adenoviral genome, and mutations also can be the insertion of one or more non-native nucleotides into the adenoviral genome. Of course, native sequences can be deleted and non-native sequences inserted to effect a replacement mutation of native adenoviral DNA (such as the insertion of a transgene into the adenoviral genome). A deficiency in a gene or gene function is a type of mutation which serves to impair or obliterate the function of the gene whose DNA sequence was mutated in whole or in part.

The present invention provides a recombinant adenovirus having a genome with a deficiency in the E1 region and a mutation in the MLP. The deficiency in the E1 region can effect E1 A, E1B, or both E1A and E1B, and recombinant viruses having such deficiencies are known in the art. Moreover, mutations of the E1 region can optionally affect the non-essential pIX gene. As is known in the art, mutations in the pIX gene reduce the packaging efficiency of large adenoviral genomes. Moreover, adenoviruses produced in the absence of the pIX gene product are more heat labile than wild-type adenoviruses. Despite these phenotypes, removal of a portion of the sequences governing pIX expression is preferred in some applications because such mutations minimize the sequence overlap between the adenoviral genome and the E1-complementing DNA of cell lines commonly used to propagate first-generation adenoviral vectors (e.g., HEK-293 cells), thus minimizing the likelihood that recombination events will generate an RCA. Preferably, the recombinant adenovirus of the present invention is at least deficient in a function provided by region E1 in combination with a deficiency in region E2 (i.e., E2A, E2B, or both E2A and E2B), and/or E3, and/or E4. More preferably, the recombinant adenovirus of the present invention comprises a deficiency in the E1 and E3 regions. While the adenovirus can have these, and other (e.g., one or more late genes (L1–L5), IVa2, etc.), deficiencies, to facilitate DNA replication and packaging of the recombinant genomes into maturing adenoviral capsids, preferably either at least the viral inverted terminal repeats and some of the promoters or at least the viral inverted terminal repeats and a packaging signal are left intact.

As mentioned, a deficiency mutation can include the insertion of, including the replacement of native sequences with, foreign DNA (i.e., DNA other than DNA native to a given serotype), which can be a foreign gene. Such a foreign gene can be under the control of a native adenoviral promoter. For example, the insertion of a foreign gene into the E2A region is facilitated by the introduction of a unique restriction site, such that the foreign gene product may be expressed from the E2A promoter. Conversely, the foreign gene can be placed under the control of a non-native promoter. In this respect, any non-native promoter can be employed to drive the expression of a non-native transcription cassette. Such promoters/enhancer elements are well known in the art. Examples of suitable promoters include prokaryotic promoters or viral promoters (e.g., retroviral inverted (intermediate) terminal repeat elements (ITRs), viral long terminal repeats (LTRs); immediate early viral promoters, such as herpesvirus IE promoters, or cytomegalovirus (CMV) IE promoters; and other viral promoters, such as Rous Sarcoma Virus (RSV) promoters, or Murine Leukemia Virus (MLV) promoters). Other suitable promoters are eukaryotic promoters, such as constitutively active promoters (e.g., the β-actin promoter), signal specific promoters (e.g., inducible and/or repressible promoters, such as a promoter responsive to tumor necrosis factor, RU-486, metallothionine, rec.), and tissue-specific promoters (e.g., those active in epidermal tissue, dermal tissue, tissue of the digestive organs (e.g., cells of the esophagus, stomach, intestines, colon, etc., or their related glands), smooth muscles, such as vascular smooth muscles, cardiac muscles, skeletal muscles, lung tissue, hepatocytes, lymphocytes (e.g., T-cells, B-cells, NK cells, etc.), endothelial cells, sclerocytes, kidney cells, glandular cells (e.g., those in the thymus, ovaries, testicles, pancreas, adrenals, pituitary, etc.), tumor cells, cells in connective tissue, cells in the central nervous system (e.g., neurons, neuroglia, etc.), cells in the peripheral nervous system, and other cells of interest).

In addition to the aforementioned deficiency in at least the E1 region, the recombinant adenovirus also has a mutation in the MLP. The mutation in the MLP can be in any of the MLP control elements (discussed above) such that it alters the responsiveness of the promoter. Preferably, the mutation renders the MLP less active within a cell other than a packaging cell. Because many of the MLP control elements are redundant, at least in the presence of the E1A gene products (i.e., the promoter functions despite mutation of the element), desirably, the mutation of the MLP implicates more than one of the MLP control elements. For example, while ablation of either the INR or the TATA box element alone does not appreciably alter MLP activity, the mutation of both the INR and TATA boxes does dampen viral growth. Similarly, viruses having altered CAAT boxes grow with normal kinetics; however, double mutant CAAT-TATA mutants are growth impaired. Thus, the mutation in the MLP desirably implicates at least two of the MLP elements. Preferably, to attenuate the promoter further, the mutation implicates three or even more of the MLP elements (e.g., four or more of the MLP elements), and the mutation can implicate even five or, indeed all of the MLP elements.

Some mutations of the MLP (e.g., certain mutations of the CAAT box), attenuate the promoter but have no appreciable effect on viral growth. An E1-deficient adenovirus having such a mutation is a suitable recombinant adenovirus of the present invention. In packaging cells (i.e., those supplying E1 gene products), the mutation of the MLP does not inhibit viral growth. However, the mutation in the MLP effectively attenuates the growth of such viruses in non-complementing cells beyond that seen for "first generation" adenoviral vectors lacking only the E1 gene products. In other embodiments, the mutation in the MLP severely curtails viral growth by greatly reducing the activity of the MLP (e.g., CAAT-UPE mutations). Such viruses can be propagated in packaging cells such as those described herein (e.g., a cell line expressing E1 and L1–L5 gene products).

Still other mutations of the MLP curtail viral growth only in non-complementing cells by altering the responsiveness of the MLP. For example, the MLP can be mutated to respond to transcription factors present within packaging cells but not present within target cells. In this light, mutations either in the TATA box such that it fails to bind the wild-type TATA-binding protein (TBP) (Wobbe et al., *Mol. Cell. Biol.* 10, 3859–67 (1990) or in an upstream sequence such that it fails to bind the USF protein do not alter the growth of resultant viruses (Reach et al., 1990, supra; Reach et al., 1991, supra). However, as mentioned, when both of these mutations are present, the growth dampening effect on the virus is lethal (Reach et al., supra). The lethality of this combination is overcome in packaging cells expressing a mutant form of the TBP that recognizes the mutant sequence (Bryant et al., *Genes Dev.*, 10, 2491–2501 (1996); Tansey et al., *Science*, 275, 829–31 (1997); see also Burley, *Nature*, 381, 112–13 (1996)). Thus, the recombinant adenovirus of the present invention can have a mutation rendering the MLP responsive to such an altered TBP.

In other embodiments, the mutation in the MLP places the MTLU under the control of an exogenous promoter. To prevent the expression of the MTLU in a host cell, the exogenous promoter desirably is not a constitutively active promoter. Thus, the exogenous promoter preferably is either an inducible promoter or a tissue specific promoter. Where the promoter is a tissue specific promoter, it preferably is not active in the desired host cell, while being active in the packaging cell. To maximize the scope of host cell types in which the recombinant adenovirus of the present invention can be employed, most preferably the exogenous promoter is an inducible promoter. The mutation in the MLP most preferably does not render the recombinant adenovirus deficient for the pol gene. Unfortunately, most inducible promoters are large and complex, and are, therefore, not likely to be successfully introduced into the adenoviral genome without destroying the pol gene. However, one suitable inducible (and cell-type specific) promoter is the NF-AT1 response element. This promoter is less than 30 nucleotides long, and introducing it into the adenoviral genome results in a mutant pol gene product, but the mutation is not so severe as to render the polymerase inoperable. The NF-AT1 response element normally responds to a factor present only in T-cells. Within T-cells, the factor is present within the cytoplasm unless induced to be transported to the nucleus, where it binds the 30-nucleotide response element to activate transcription (see Loh et al., *J. Biol. Chem.*, 271, 10884–91 (1996)). Thus, in most cell types, the recombinant adenovirus having the exogenous NF-AT1 response element will not express the L1–L5 genes.

The effects of the MLP mutations on the activity of the MLP can be assessed by any suitable method. For example, an RNAse protection assay can detect the relative activity of the promoter at various time courses. However, the results of an RNAse protection assay do not necessarily correlate with the effect of a given MLP mutation on viral growth (see, e.g., Reach et al., 1991, supra). Thus, in addition to promoter activity, the effect of a given MLP mutation on viral growth desirably is assayed. Methods for assaying adenoviral growth are well known in the art. As mentioned, the products of the major late genes lie on the chromosomal strand directly opposite the pol coding sequence. Thus, any assay for viral growth should include, as a control, cells expressing the adenoviral pol gene to dissect the effect of the mutated MLP on viral growth from any effect of an alteration of the pol gene.

While the mutation alters the activity of the MLP, preferably, the mutation does not result in a deficiency in the pol gene, which as mentioned, lies on the chromosomal strand directly opposite the MLP. This is preferred to avoid the use of cell lines complementing the pol gene, as such cell lines can result in the production of RCAs. Of course, additions or deletion mutations in the MLP elements should not introduce frame-shift mutations into the pol coding sequence. Many mutations of the MLP elements can be made without altering the pol amino acid sequence. Other mutations adding or deleting one or a few amino acids of the pol sequence do not result in deficiencies (see, e.g., Reach et al., 1990, supra; Reach et al., supra, 1991; Lu et al., 1997, supra). Indeed, even if the pol product is somewhat impaired by a mutation, the virus nonetheless can be viable as the pol product is needed only at catalytic (e.g., relatively low amounts), as opposed to stoichiometric, levels. A convenient assay for assessing whether a given mutation results in a deficiency of the pol gene is to assess whether the pol gene product must be complemented for the virus to grow, for example using cell lines such as those described herein.

The recombinant adenovirus of the present invention can be produced by any suitable method, many of which are known in the art (see, e.g., Berkner et al., *Nucl. Acids Res.*, 12, 925–941 (1984); Berkner et al., *Nucl. Acids Res.*, 11, 6003–6020 1983); Brough et al., *Virol.* , 190, 624–634 (1992)). A typical method for producing recombinant adenoviruses, however, is to employ homologous recombination within a suitable host cell. In this method, a cassette having an adenoviral gene or region with the desired mutation (e.g., within the MLP) is first generated by standard molecular biological techniques. This altered DNA is then cloned into a much larger plasmid containing a large portion (e.g., up to about one half) of the adenovirus genome. The next step is to transfect the plasmid DNA (containing the deletion or modification) and other DNA containing the remainder of the adenoviral genome into a recipient cell. Together these pieces of DNA encompass all of the adenovirus genome plus regions of similarity. Within theses regions of similarity, recombination events will take place to generate a recombed viral genome having the deletion or modification. The recipient cell should provide not only the recombination functions but also all missing viral functions not contained within the transfected viral genome, thus complementing any deficiencies of the recombined viral genome. The adenovirus can be further modified by alteration of the ITR and/or packaging signal, for example, so that the recombinant virus only functions or grows in a complementing cell line.

Generally, the recombinant adenovirus of the present invention is most useful when enough of the virus can be delivered to a host cell population to ensure that the cells are confronted with a certain number of viruses. Thus, the present invention provides a stock of recombinant adenovirus, preferably an RCA-free stock of recombinant adenovirus. The preparation and analysis of adenovirus stocks is well known in the art. Viral stocks vary considerably in titer, depending largely on viral genotype and the protocol and cell lines used to prepare them. The viral stocks of the present invention can have a titer of at least about $10^7$ pfu (such as about $10^8$ pfu), and many such stocks can have higher titers, such as at least about $10^9$ pfu or even at least about $10^{11}$ pfu (e.g. about $10^{12}$ pfu). Depending on the nature of the recombinant virus and the packaging cell line, it is possible that a viral stock of the present invention can have a titer of even about $10^{13}$ pfu or higher. Preferably, a viral stock of the present invention is composed of at least about 90% of one to about four viral vectors. That is, the inventive viral stocks are substantially free of contaminating viruses, regardless of the replication competency of the contaminating virus.

As mentioned, the recombinant adenoviruses of the present invention can be used to study viral gene regulation. Alternatively, as mentioned, the recombinant adenovirus of the present invention can have non-native genes; thus, they are useful expression vectors. In either application, the virus (or viral stock) is transferred to the desired target cell (i.e., host cell) under conditions appropriate for the virus to productively infect the cell. Where the titer of a viral stock is known, a predetermined amount of the virus can be supplied to the desired target (e.g., a desired m.o.i.).

For delivery to a desired cell, a recombinant adenovirus (or viral stock) of the present invention can be incorporated into a suitable carrier. As such, the present invention provides a composition comprising a recombinant adenovirus of the present invention and a suitable carrier. Where the host cell is within an animal, preferably the carrier is a pharmacologically acceptable carrier to minimize the deleterious effects of the protocol on the host. Any suitable preparation is within the scope of the invention; the exact formulation, of course, depends on the nature of the desired application (e.g., target cell type, mode of administration, etc.), and is within the purview of those of skill in the art. Accordingly, a wide variety of suitable formulations are available for use in the context of the present invention, many types of which are described elsewhere, for example, in published international application WO 95/34671.

Desirably, a packaging cell line is employed to propagate the recombinant adenovirus of the present invention, as well as to produce the inventive viral stocks. Many cell lines able to complement the essential adenoviral E1 gene products are known in the art (e.g., HEK-293 cells, A594 cells, Per.C6 cells, etc.), and any of these lines are suitable for propagating viruses of the present invention not deficient in essential viral genes other than the E1 genes. Additionally, to assess the specificity of some mutations on the MLP, as opposed to the pol gene. an E1/pol complementing cell line can be employed, and such cell lines are known in the art (Almafitano et al., 1996, supra). While the mutations in the MLP preferably do not significantly impair the pol gene. such cell lines can be used to propagate recombinant viruses in which the pol gene is impaired. The present invention provides complementing cell lines to propagate adenoviruses which require factors other than the E1 gene products.

The cell lines of the present invention complement all essential functions missing from the recombinant adenovirus of interest (i.e., genes within the E1 region as well as any other essential adenoviral genes, such as those genes described herein). Such cells are generated using standard molecular biological techniques, for example, as described in published international patent application WO 95/34671. Preferably, the cell lines contain multiple complementing genes in a non-overlapping fashion, which reduces or substantially eliminates the possibility of the viral genome recombining with the cellular DNA to produce RCAs. The complementing cell line desirably expresses the complementing gene products at a level appropriate to generate a high titer stock of recombinant adenovirus. For example, the E2A product, DBP, should be expressed at stoichiometric levels (i.e., relatively high levels) for adenoviral DNA replication, while other gene products are necessary at only catalytic levels (i.e., relatively low levels). In addition, the temporal expression of the product desirably is consistent with that seen in normal viral infection of a cell. For example, the components necessary for viral DNA replication must be expressed before those necessary for virion assembly. To minimize or avoid cellular toxicity from the presence of the viral products, and to regulate the temporal expression of the products, inducible promoter systems are desirably used. For example, the sheep metallothionine inducible promoter system can be used to express the complete E4 region, the open reading frame 6 of the E4 region, and/or the E2A region. Other examples of suitable inducible promoter systems include, but are not limited to, the bacterial lac operon, the tetracycline operon, the T7 polymerase system, and combinations and chimeric constructs of eukaryotic and prokaryotic transcription factors, repressors, and other components. Where the viral product to be expressed is highly toxic, a bipartite inducible system, wherein the inducer is carried in a viral vector and the inducible product is carried within the chromatin of the complementing cell line, further controls expression.

Cell lines of the present invention can express one or more factors (e.g., transcription factors) binding the MLP. The cell line can be engineered to produce DEF-A or DEF-B proteins or factors binding a MLP modified as discussed herein. For example, where the MLP has an altered TATA box, the cell line can express a mutant form of the TBP (e.g., TBPm3e) that recognizes the mutant TATA sequence (Bryant et al., supra; Tansey et al., supra; Burley, Nature, supra). Similarly, cells can be engineered to express the NF-AT1 gene to propagate recombinant adenoviruses having the NF-AT1 response element. Cell lines used to propagate E1-deficient adenoviruses (e.g., HEK-293 cells, A549 cells, Per.C6 cells, etc.) do not express either the TBPm3e or NF-AT1 gene. However, the sequences for these genes are known, and cDNA is available ((Bryant et al., supra; Tansey et al., supra; Burley, Nature, supra; Loh et al., supra, van Beveren et al., supra). Thus, the cDNA can be engineered into an appropriate vector (e.g., containing a selectable marker) for introduction into a suitable E1-complementing cell line. Such a cell line is able to propagate an adenovirus having an exogenous response element operably linked to the MTLU.

Another cell line of the present invention expresses the essential E1A products and also the L1–L5 gene products. Such a cell line is useful for propagating recombinant adenoviruses of the present invention having a mutation in the MLP that severely curtails viral growth by greatly reducing the activity of the MLP. Preferably, the L1–L5 DNA coding regions within such packaging cells are linked to a promoter (or promoters if the genes are within separate cassettes) other than an MLP promoter. The use of such non-MLP promoters to drive complementary L1–L5 gene products minimizes the likelihood that recombination events will occur between the viral genome and the complementary DNA. Moreover, the use of such non-MLP promoters minimizes the risk that any such recombination would result in a viable virus because such DNA sequences, if recombined into the viral genome, would likely render any resultant virus deficient for the pol gene product.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A recombinant cell line, which produces adenoviral E1 and DEF-A or DEF-B gene products.

2. The recombinant cell line of claim 1, which produces the DEF-A gene product.

3. The recombinant cell line of claim 1, which produces the DEF-B gene product.

4. The recombinant cell line of claim 1, which produces the DEF-A and the DEF-B gene product.

* * * * *

SEQUENCE LISTING

<160> NUMBER OF SEQ ID NOS: 4

<210> SEQ ID NO 1
<211> LENGTH: 15
<212> TYPE: DNA
<213> ORGANISM: Adenovirus type 5

<400> SEQUENCE: 1
tcctcactct cttcc                                                    15

```
<210> SEQ ID NO 2
<211> LENGTH: 12
<212> TYPE: DNA
<213> ORGANISM: Adenovirus type 5

<400> SEQUENCE: 2
ggccacgtga cc                                                              12

<210> SEQ ID NO 3
<211> LENGTH: 11
<212> TYPE: DNA
<213> ORGANISM: Adenovirus type 5

<400> SEQUENCE: 3
ttgtcagttt c                                                               11

<210> SEQ ID NO 4
<211> LENGTH: 15
<212> TYPE: DNA
<213> ORGANISM: Adenovirus type 5

<400> SEQUENCE: 4
aacgaggagg attga                                                           15
```